US006663857B1

(12) United States Patent
Barba et al.

(10) Patent No.: US 6,663,857 B1
(45) Date of Patent: *Dec. 16, 2003

(54) IN VIVO GENE TRANSFER USING IMPLANTED RETROVIRAL PRODUCER CELLS

(75) Inventors: David Barba, San Diego, CA (US); Fred H. Gage, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/242,193

(22) Filed: May 13, 1994

Related U.S. Application Data

(63) Continuation-in-part of application No. 07/744,335, filed on Aug. 13, 1991, now Pat. No. 5,529,774.

(51) Int. Cl.$^7$ .................. A01N 63/00; A01N 43/04; A61K 48/00; A61K 31/70
(52) U.S. Cl. ................. 424/93.21; 424/93.6; 424/93.2; 514/44; 435/320.1
(58) Field of Search .................. 514/44; 424/93.2, 424/93.21, 93.6; 435/320.1

(56) References Cited

FOREIGN PATENT DOCUMENTS

| EP | 0415731 A2 * | 3/1991 |
|---|---|---|
| WO | WO 90/06757 | 6/1990 |
| WO | WO93/03743 | 3/1993 |
| WO | WO 93/21959 | 11/1993 |

OTHER PUBLICATIONS

Huber etal (1993) Canc. Res. 53, 4619–4626.*
Colambo et al (1995) Human Gene Therapy 6, 763–772.*
Barba etal (1994) Proced. Nat. Acad. Sci 91, 4348–4352.*
Muelen (1994) Pharmac. Therap. 63, 199–207.*
Blau et al (Nov. 2, 1995) New Eng. J. Med.,1204–1207.*
Vieweg et al (1995) Cancer Invest. 13, 193–201.*
Report and Recommendations of the Panel to Assess the NIH Investment in Research on Gene Therapy, Orkin et al, Dec. 7, 1995.*
Moolten & Brodeur, Proc. Am. Assoc. *Cancer Res.* 29:461 (1988) (Exhibit 17).
Friedmann, *Gene Therapy Fact and Fiction*, Cold Spring Harbor Laboratory, New York (1983) (Exhibit 18).
Z.D. Ezzedine et al. (Jun. 1991) "Selective killing of glioma cells in culture and in vivo by retrovirus transfer of the herpes simplex virus thymidine kinase gene" The New Biologist 3(6):608–614.
Short et al. (1990) "Gene delivery to glioma cells in rat brain by grafting of a retrovirus packaging cell line:" Journal of Neuroscience Research 27:427–433.
Rosenstein, J.M., "Neocortical Transplants in the Mammalian Brain Lack a Blood–Brain Barrier to Macromolecules," *Science* 235:772–774 (1987) (Exhibit 1).

Anderson, W.F., "Prospects for Human Gene Therapy," *Science* 226:401–409 (1984) (Exhibit 2).
Friedmann, T. & Roblin, R., "Gene Therapy for Human Genetic Disease?", *Science* 175:949–955 (1972) (Exhibit 3).
Rosenberg, S.A. et al., "A New Approach to the Adoptive Immunotherapy of Cancer With Tumor–Infiltrating Lymphocytes," *Science* 233:1318–1321 (1986) (Exhibit 4).
Wolff, J.A., et al., "Grafting fibroblasts genetically modified to produce L–dopa in a rat model of Parkinson disease," *Proc.Natl.Acad. Sci.USA* (1989) 86:9011–9014 (Exhibit 5).
Moolten, F.L. et al., "Curability of Tumors Bearing Herpes Thymidine Kinase Genes Transferred by Retroviral Vectors," *Journal of the National Cancer Institute, REPORTS* 82 (4):297–300 (1990) (Exhibit 6).
Moolten, F.L., "Tumor Chemosensitivity Conferred by Inserted Herpes Thymidine Kinase Genes: Paradigm for a Prospective Cancer Control Strategy," *Cancer Research* 46:5276–5281 (1986) (Exhibit 7).
Gage, F.H. et al., "Implantation of genetically engineered cells to the brain," *Progress in Brain Research* 78:651–658 (1988) (Exhibit 8).
Yee, J.–K. et al., "Gene Expression from a Transcriptionally Disabled Retroviral Vector," *Cold Spring Harbor Symposia on Quantitative Biology* 51:1021–1026 (1986) (Exhibit 9).
Wolff, J.A. et al., "Expression of retrovirally transduced genes in primary cultures of adult rat hepatocytes," *Proc.Natl.Acad.Sci.USA* 84:3344–3348 (1987) (Exhibit 10).
Jolly, D.J. et al., "Cell Targeting Techniques—High Efficiency Gene Transfer into Cells" *Methods In Enzymology* 149:10–25 (1987) (Exhibit 11).
Miller, A.D. et al., "Generation of Helper–Free Amphotropic Reroviruses That Transduce a Dominant–Acting, Methotrexate–Resistant Dihydrofolate Reductase Gene," *Molecular And Cellular Biology* 5(3):431–437 (1985) (Exhibit 12).

(List continued on next page.)

*Primary Examiner*—Deborah Crouch
(74) *Attorney, Agent, or Firm*—Mandel & Adriano

(57) ABSTRACT

The present invention is directed to methods of transferring therapeutic genes to brain tumor cells in order to kill the cells. In general, the method of the present invention comprises: (1) introducing a retrovirus containing a selectable marker and at least one gene required for its replication into producer cells such that integration of the proviral DNA corresponding to the retrovirus into the genome of the producer cell results in the generation of a modified retrovirus wherein at least one of the genes required for replication of the retrovirus is replaced by the therapeutic gene or genes; (2) selecting producer cells in which the modified retrovirus is incorporated as part of the genome of the producer cells; (3) grafting the producer cells in proximity to the dividing tumor cell in order to infect the tumor cell with the modified retrovirus, thereby transferring the therapeutic gene or genes to the tumor cell; and (4) killing the cells by administering a substance that is metabolized by the therapeutic gene transferred to the tumor cells into a metabolite that kills the cells. Suitable retroviral vectors and methods for generating them, producer cells, and grafting methods are described.

5 Claims, 8 Drawing Sheets

OTHER PUBLICATIONS

Eglitis, M.A. & Anderson, W.F., "Retroviral Vectors for Introduction of Genes into Mammalian Cells," *BioTechniques* 6(7):608–614 (1988) (Exhibit 13).

Bender, M.A. et al., "Evidence that the Packaging Signal of Moloney Murine Leukemia Virus Extends into the gag Region," *Journal Of Virology* 61(5):1639–1646 (1987) (Exhibit 14).

Howell, S.B. et al., "Gene Therapy for Thioguanine–resistant Human Leukemia," *Mol.Biol.Med.* 4:157–168 (1987) (Exhibit 15).

Das, G.D., "Intraparenchymal Transplantation," *Neural Grafting in the Mammalian CNS* 3:23–30 (1985) (Exhibit 16).

Freed, W.J., "Transplantation of Tissues to the Cerebral Venricles: Methodological Details and Rate of Graft Survival," *Neural Grafting in the Mammalian CNS* 4:31–40 (1985) (Exhibit 17).

Brundin, P. et al., "Intracerebral Grafts of Neuronal Cell Suspensions," *Neural Grafting in the Mammalian CNS* 6:51–59 (1985) (Exhibit 18).

David, S. & Aguayo, A.J., "Peripheral Nerve Transplantation Techniques to Study Axonal Regeneration From the CNS of Adult Mammals," *Neural Grafting in the Mammalian CNS* 7:61–69 (1985) (Exhibit 19).

Seiger, A., "Preparation of Immature Central Nervous System Regions for Transplantation," *Neural Grafting in the Mammalian CNS* 8:71–77 (1985).

Mann, R. et al., "Construction of Retrovirus Packaging Mutant and Its Use to Produce Helper–Free Defective Retrovirus," *Cell* 153–159 (1983) (Exhibit 21).

Shimohama, S. et al., Grafting genetically modified cells into the rat brain: characteristics of *E coli* β–galactosidase as a reporter gene (1989) 5:271–278 (Exhibit 22).

Culver, K.W. et al., "In Vivo Gene Transfer with Retroviral Vector–Producer Cells for Treatment of Experimental Brain Tumor," *Science* 256:1550–1552 (1992) (Exhibit 23).

Ram, Z. et al., "In Situ Retroviral–mediated Gene Transfer for the Treatment of Brain Tumors in Rats," *Cancer Research* 53:83–88 (1993) (Exhibit 24).

* cited by examiner

IN VIVO GENE TRANSFER USING IMPLANTED RETROVIRAL PRODUCER CELLS

This application is a continuation-in-part of U.S. Ser. No. 07/744,335, filed Aug. 13, 1991, now U.S. Pat. No. 5,529,774 the contents of which are incorporated by reference into the present application.

TECHNICAL FIELD OF THE INVENTION

The present invention relates to the use of recombinant DNA technology for in vivo gene transfer using implanted retroviral producer cells. Specifically, the invention relates, to the therapy of brain tumors using modified producer cells to make brain tumor cells sensitive to chemotherapeutic agents.

BACKGROUND OF THE INVENTION

Brain tumors are major causes of morbidity and mortality, particularly among young people. Moreover, their incidence appears to be increasing for unknown reasons. The causes of brain tumors are not known, although radiation, pollutants, and electromagnetic fields are suspected. Most brain tumors are inoperable; even for those brain tumors that are operable, operations to remove them are extremely difficult and delicate and frequently leave neurological deficits. There is a need for more efficient chemotherapeutic treatment of brain tumors.

One possible avenue of treatment for brain tumors, as yet little explored, involves intracerebral neural grafting of cells that produce anti-cancer agents. This may offer the advantage of averting repeated drug administration while also avoiding the drug delivery complications posed by the blood-brain barrier. (Rosenstein, *Science* 235:772–774 (1987)).

As these critical factors have become recognized and optimized, intracerebral grafting has become a valid and reliable tool for neurobiologists in the study of CNS function and potentially for clinicians for the design of therapies of CNS disease, including brain tumors.

In parallel to the progress in neurobiology during the past several decades, advances in the understanding of molecular biology and the development of sophisticated molecular genetic tools have provided new insights into human disease in general. As a result, medical scientists and geneticists have developed a profound understanding of many human diseases at the biochemical and genetic levels. The normal and abnormal biochemical features of many human genetic diseases-have become understood, the relevant genes have been isolated and characterized, and early model systems have been developed for the introduction of functional wild-type genes into mutant cells to correct a disease phenotype. (Anderson, *Science* 226:401–409 (1984)). The extension of this approach to whole animals, that is, the correction of a disease phenotype in vivo through the use of the functional gene as a pharmacologic agent, has come to be called "gene therapy". (Friedmann et al., *Science* 175:949–955 (1972); Friedmann, *Gene Therapy Fact and Fiction*, Cold Spring Harbor Laboratory, New York (1983)). Gene therapy is based on the assumption that the correction of a disease phenotype can be accomplished either by modification of the expression of a resident mutant gene or the introduction of new genetic information into defective or damaged cells or organs in vivo.

Procedures for in vivo gene therapy have been described. See, e.g., Rosenberg et al., *Science* 242:1575–1578 (1988), and Wolff et al., *Proc. Natl. Acad. Sci. USA* 86:9011–9014 (1989), both incorporated herein by this reference, as well as co-pending U.S. patent application Ser. No. 07/285,196 by Gage, entitled "Method of Grafting Genetically Modified Cells to Treat Defects, Disease or Damage of the Central Nervous System," filed Dec. 15, 1988, and incorporated herein by this reference.

The anti-viral agents acyclovir (9-((2-hydroxyethoxy)methyl)guanine) and ganciclovir (9-((2-hydroxy-1-(hydroxymethyl)ethoxy)methyl)guanine) are efficient for preventing the replication of herpes virus, as the thymidine kinase coded for by the herpes virus genome and produced in cells infected by the herpes virus (HSV-TK) converts these drugs into intermediates capable of inhibiting DNA synthesis in vivo. Transfer of HSV-TK into tumor cells by retroviral vectors has been shown to mediate tumor regression from mouse sarcomas (Moolten & Wells, *J. Natl. Cancer Inst.*, 82:297–300 (1990)) and to prevent growth of neoplastic BALB/c murine cell lines (Moolten, *Cancer Res.* 46:527–581 (1986)).

It would be advantageous to develop procedures for gene transfer via efficient vectors into cells followed by intracerebral grafting of genetically modified cells in vivo to treat brain tumors by introduction of therapeutic genes such as HSV-TK into the tumors.

SUMMARY

The present invention provides methods for transferring therapeutic genes to brain tumor cells in order to kill the cells. In general, the method of the present invention comprises:

(1) introducing a retrovirus containing a selectable marker and at least one gene required for replication of the retrovirus into producer cells such that integration of the proviral DNA corresponding to the retrovirus into the genome of the producer cells results in the generation of a modified retrovirus wherein at least one of the genes required for replication of the retrovirus is replaced by the therapeutic gene or genes;

(2) selecting producer cells in which the modified retrovirus is incorporated as part of the genome of the producer cells;

(3) grafting the producer cells in proximity to the dividing tumor cells in order to infect the tumor cells with the modified retrovirus, thereby transferring the therapeutic gene or genes to the tumor cells; and (4) killing the cells by administering a substance that is metabolized by the therapeutic gene or genes transferred to the tumor cells into a metabolite that kills the cells.

The tumor cells can be glioma cells. One of the genes transferred can be herpes simplex thymidine kinase (HSV-TK). The substance can be selected from the group consisting of: 9-((2-hydroxyethoxy)methyl)guanine and 9-((2-hydroxy-1-(hydroxymethyl)ethoxy)methyl)guanine. A preferred retroviral vector for transferring HSV-TK can contain a NeoR gene and a control element selected from the group consisting of the thymidine kinase promoter, the SV40 early region promoter-enhancer, and the immunoglobulin heavy chain enhancer. The retrovirus can be derived from the Moloney murine leukemia virus.

More specifically, the invention comprises a method of preventing replication of tumor cells in vivo comprising:

(1) introducing a retroviral vector containing a selectable marker and the gene for herpes simplex thymidine kinase into producer cells such that integration of proviral DNA corresponding to the retroviral vector into the genome of the producer cell results in generation of a modified retrovirus wherein at least one of the genes required for replication of the retrovirus is replaced by the herpes simplex thymidine kinase gene;

(2) selecting producer cells carrying the herpes simplex thymidine kinase gene;

(3) grafting the producer cells carrying the modified retrovirus in proximity to the tumor cells in order to infect the tumor cells with the modified retrovirus, thereby transferring the herpes simplex thymidine kinase gene to the tumor cell; and (4) administering an anti-cancer agent selected from the group consisting of: 9-((2-hydroxyethoxy)methyl) guanine and 9-((2-hydroxy-1-(methyl)ethoxy)methyl) guanine such that the herpes simplex thymidine kinase gene metabolizes the anti-cancer agent into a metabolite that blocks replication of the tumor cells.

DETAILED DESCRIPTION OF THE INVENTION

Figure 1:
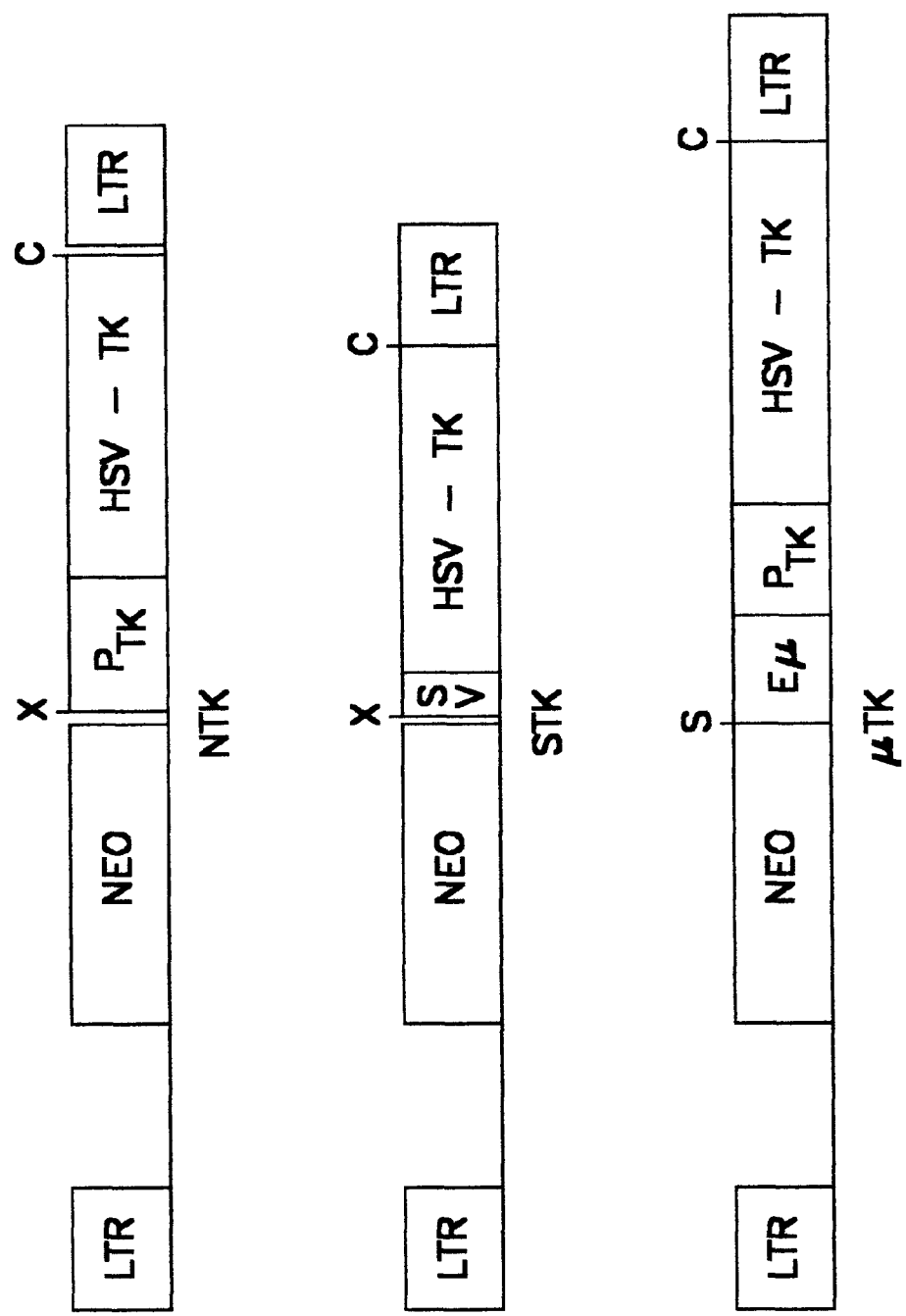
FIG. 1 is a diagrammatic representation of the linear restriction maps of the integrated vectors NTK, STK, and αTK, each carrying the herpes simplex virus thymidine kinase gene (LTR=long terminal repeat; HSV-TK=herpes simplex virus thymidine kinase gene; NEO=NeoR gene; X=Xho I site; C=Cla I site; S=Sal I site; $P_{TK}$=HSV-TK promoter; SV=SV40 promoter-enhancer; Eμ=immunoglobulin heavy chain enhancer).

In order that the invention herein described may be more fully understood, the following detailed description is set forth. The present invention relates to a process for transfer of at least one selected therapeutic gene to human tumor cells in vivo in order to alter their phenotype or behavior for anti-tumor therapy. More particularly, the invention relates to a method of treating human tumors by implanting genetically modified retroviral producer cells, defined herein as cells carrying a retrovirus incorporating a therapeutic gene and capable of producing replication-defective retrovirus that can infect neighboring cells and thereby transfer the therapeutic gene or genes. These retroviral producer cells carry a modified defective retrovirus in which at least one of the genes required for replication of the retrovirus is replaced by the therapeutic gene or genes. The producer cells then produce the defective retrovirus and infects the neighboring tumor cells, thereby transferring the therapeutic gene or genes to the infected neighboring tumor cells. Typically, the tumor cells are then killed by administering a substance that is metabolized by one of the therapeutic genes transferred to the tumor cells into a tumoricidal metabolite.

For example, the retroviral producer cells can carry a retroviral vector containing the gene for the enzyme herpes simplex virus thymidine kinase (HSV-TK). This gene renders cells carrying it susceptible to the DNA synthesis-inhibiting drugs acyclovir (9-((2-hydroxyethoxy)methyl) guanine)) or its analog ganciclovir (9-((2-hydroxy-1-(hydroxymethyl)ethoxy)methyl)guanine). These drugs are specifically converted by the herpes simplex thymidine kinase to intermediates capable of inhibiting the DNA synthesis of the cell, thus rendering cells carrying the genes susceptible to administration of the drug and leading to tumor cell death after its administration.

I. Gene Transfer Into Donor Cells In Vitro

A general strategy for transferring genes into donor cells using retroviral vectors in vitro has been described (Gage et al., Ch. 86, In Progress in Brain Research, Vol. 78, pp. 651–658, 1988, incorporated herein by this reference, and co-pending U.S. patent application Ser. No. 07/285,196 by Gage, supra) and includes the following basic steps:

(1) Selection of appropriate therapeutic genes whose expression is correlated with the desired phenotypic effect;

(2) Development of suitable and efficient vectors for gene transfer;

(3) Preparation of donor cells from primary cultures or from the established cell lines;

(4) Demonstration that donor-implanted cells expressing the new phenotype in vivo are viable and can express the therapeutic gene products stably and efficiently, and can transfer the gene to cells in proximity to the implanted cells;

(5) Demonstration that transplantation causes no serious deleterious effects; and (6) Demonstration of the desired phenotypic effect in the host animal, such as sensitivity of the tumor cells to the drug.

A. Genetic Modification of Donor Cells

The methods described below to genetically modify donor cells using retroviral vectors and grafting into the brain are merely for purposes of illustration and are typical of those that might be used. However, other procedures may also be employed, as is understood in the art.

Most of the techniques used to transform cells, construct vectors and the like are widely practiced in the art, and most practitioners are familiar with the standard resource materials which describe specific conditions and procedures. However, for convenience, the following paragraphs may serve as a guideline.

1. Choice of Vector

Although other vectors may be used, preferred vectors for use in the method of the present invention are viral (including retroviral) vectors. The viral vectors should meet the following criteria:

(1) The vector must be able to infect donor cells and thus viral vectors having an appropriate host range must be selected;

(2) The vector must be readily selectable so that donor cells carrying it can be isolated and cloned; and (3) The vector should do little, if any, damage to target cells other than the tumor cells against which the transferred tumoricidal gene is directed.

Murine retroviral vectors offer an efficient, useful, and presently the best-characterized means of introducing and expressing the foreign genes efficiently in mammalian cells. These vectors have very broad host and cell type ranges, integrate by reasonably well understood mechanisms into random sites in the host genome, express genes stably and efficiently, and under most conditions do not kill or obviously damage their host cells.

2. General Methods of Vector Construction

Construction of suitable vectors containing the desired therapeutic gene coding and control sequences employs standard ligation and restriction techniques which are well understood in the art (see Sambrook, Fritsch, and Maniatis, in *Molecular Cloning: A Laboratory Manual*, Cold Spring Harbor Laboratory, New York (2d ed., 1989)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes. (See, e.g. New England Biolabs, Product Catalog.) In general, about 1 $\mu$g of plasmid or DNA sequences is cleaved by one unit of enzyme in about 20 $\mu$l of buffer solution. Typically, an excess of restriction enzyme. is used to insure complete digestion of the DNA substrate.

Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* 65:499–560 (1980).

Restriction cleaved fragments may be blunt ended by treating with the large fragment of *E. coli* DNA polymerase I (the Klenow fragment) in the presence of the four deoxyribonucleotide triphosphates (dNTPs) using incubation times of about 15 to 25 min at 20° C. to 25° C. in 50 mM Tris (pH 7.6), 50 mM NaCl, 6 mM $MgCl_2$, 6 mM DTT and 5–10 $\mu$M dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with the Klenow fragment, the mixture is extracted with phenol/chloroform and ethanol precipitated. Treatment under appropriate conditions with $S_1$ nuclease or Bal-31 results in hydrolysis of any single-stranded portion.

Ligations are performed in 15–50 $\mu$l volumes under the following standard conditions and temperatures: 20 mM Tris-HCl pH 7.5, 10 mM $MgCl_2$, 10 mM DTT, 33 mg/ml BSA, 10 mM-50 mM NaCl, and either 40 $\mu$M ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 $\mu$g/ml total DNA concentrations (5–100 nM total end concentration). Intermolecular blunt end ligations (usually employing a 10–30 fold molar excess of linkers) are performed at 1 $\mu$M total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of $Na^+$ and $Mg^{2+}$ using about 1 unit of BAP or CIP per mg of vector at 60° C. for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

For portions of vectors derived from cDNA or genomic DNA which require sequence modifications, site-specific primer directed mutagenesis is used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Methods of preparation of retroviral vectors have been described (Yee et al., Cold Spring Harbor *Symp. on Quant. Biol. Vol.* LI, pp. 1021–1026 (1986); Wolff et al., *Proc. Natl. Acad. Sci. USA* 84:3344–3348 (1987); Jolly et al., *Meth. in Enzymol.* 149:10–25 (1987); Miller et al., *Mol. Cell. Biol.* 5:431–437 (1985); and Miller, et al., *Mol. Cell. Biol.* 6:2895–2902 (1986) and Eglitis et al., *Biotechniques* 6:608–614 (1988)) and are now in common use in many laboratories. Retroviral vectors contain retroviral long terminal repeats (LTRS) and packaging (psi) sequences, as well as plasmid sequences for replication in bacteria and may include other sequences such as the SV40 early promoter and enhancer for potential replication in eukaryotic cells. Much of the rest of the viral genome is removed and replaced with other promoters and genes. Vectors are packaged as RNA in virus particles following transfection of DNA constructs into packaging cell lines. These include psi ( )2 which produce viral particles that can infect rodent cells and AM and PA 12 which produce particles that can infect a broad range of species.

In a preferred viral vector the therapeutic gene or genes are brought under the control of either the viral LTR promoter-enhancer signals or of an internal promoter, and retained signals within the retroviral LTR can still bring about efficient integration of the vector into the host cell genome. To prepare transmissible virus, recombinant DNA molecules of such defective vectors are transfected into "producer" cell lines that contain a provirus expressing all of the retroviral functions required for packaging of viral transcripts into transmissible virus particles, but lacking the crucial packaging signal for encapsidation of RNA transcripts of the provirus into mature virus particles. These include the group specific antigen (qaq) and envelope (env) genes which encode capsid proteins and reverse transcriptase (pol). Because of this deletion, transcripts from the helper cannot be packaged into viral particles and the producer cells, therefore, generate only empty virus particles. However, an integrated defective retroviral vector introduced into the same cell by means of calcium phosphate-mediated transfection (Graham and Vander Eb, *Virol.* 52:456–467 (1973)) in which the qaq, env, and pol genes have been replaced by the therapeutic gene (x) with the intact psi sequence, produces transcripts that can be packaged in trans since they do contain the packaging sequence. The cells contain 2 provirus sequences integrated into different sites of the host cell genome. Because RNA transcripts from the newly introduced provirus contain the packaging sequence they are efficiently encapsidated into virus particles by means of viral functions produced in trans. Ideally, the result is the production by the cells of infectious particles carrying the therapeutic gene free of replication-competent wild-type helper virus. In most, but not necessarily all models of gene therapy, the production of helper virus is probably undesirable since it may lead to spreading infection and possibly proliferative disease in lymphoid or other tissue in the host animal.

Preferably, in retroviral vectors suitable for use in processes according to the present invention, integration of proviral DNA corresponding to the retroviral vector into a genome of the producer cell results in regeneration of a modified (defective) retrovirus wherein at least one of the genes required for replication is replaced by the gene to be transferred.

Since herpes viruses are capable of establishing a latent infection and an apparently non-pathogenic relationship with some neural cells, herpes based vectors, e.g. HSV-1, may be used. Similarly, it should be possible to take advantage of an eventual improved understanding of other human and animal viruses that infect cells of the CNS efficiently, such as rabies virus, measles, and other paramyxoviruses and the human immunodeficiency retrovirus (HIV), to develop useful delivery and expression vectors. In most cases, with the exception of rabies virus, these viruses are not truly neurotropic for infection, but rather have a much more general susceptible host cell range. They seem, rather, to appear to be neurotropic because the metabolic and physiological effects of infection are most pronounced in cells of the CNS. It is, therefore, likely that many vectors derived from these viruses will be similarly promiscuous in their cell range, and that CNS specificity for expression must be conferred by the use of appropriate cell-specific enhancer, promoter and other sequences, such as those that regulate the oligodendroglial-specific expression of JC virus, glial-specific expression of the proteolipid protein and glial fibrillary acidic protein (GFAP) genes, and other possible CNS specific functions in the mouse.

Other virus vectors that may be used for gene transfer into cells for treatment of brain tumors include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia; rabies and poliovirus and other human and animal viruses.

Particularly suitable retroviral vectors for the process of the present invention are described in Moolten & Wells, *J. Natl. Cancer Inst.*, 82:297–300 (1990), incorporated by reference herein. These vectors retain the LTR terminal repeats of the retrovirus, contain a NeoR gene that confers resistance to the neomycin analog G418, and have the HSV-TK gene under the control of a control element. In the NTK vector, the control element is the HSV-TK promoter itself. In the STK vector, the control element is the SV40 early region promoter and enhancer. In the gTK vector, the control element is the immunoglobulin heavy chain enhancer.

In the construction of these vectors, an HSV-TK sequence derived from the construct pTK is inserted in pLNL6 (Bender et al., *J. Virol.*, 61:1639–1646 (1987) which contains the NeoR gene. The construction of pTK involves excising an HSV-TK coding region segment from PLPMKL (Howell et al., *Mol. Biol. Med.*, 4:157–168 (1987)) with Bql II and Cla I restriction endonucleases, addition of Xho I linkers to the Cla I cleavage site, and insertion into the BQl II-Xho I site of P6 (Moolten & Brodeur, *Proc. Am. Assoc.*

Cancer Res., 29:461 (1988)) to join it to the HSV-TK promoter. From this, the promoter encoding sequences were excised with Bam HI and Xho I and inserted into the plasmid pBR322 after digestion of the latter with Hind III (followed by Xho I linker addition) and with Bam HI.

To construct the NTK vector, a fragment is excised from pTK by digestion with Bam HI (followed by fill-in of the single-stranded region with dATP and dGTP), and with Cla I was inserted into pLN6 digested with Xho I (followed by fill-in of the single-stranded region with dCTP and dGTP) and with Cla I.

To construct the STK vector, a Bql II-Eco RI fragment of pTK was inserted into the plasmid pUC 13. From this the HSV-TK coding sequence was excised with Hind III and Cla I and ligated to a Hind III-Cla I fragment of PLSDL (Miller et al., Mol. Cell. Biol., 5:431–437 (1985)) containing the SV40 early region promoter and enhancer.

A fragment derived from this ligation by digestion by Bam HI (followed by fill-in with dATP and dGTP) and with Cla I was inserted into pLN6 digested with Xho I (followed by fill-in with dCTP and dGTP) and with Cla I.

To construct the gTK vector, the immunoglobulin heavy chain enhancer in a fragment bounded by a completely filled-in Eco RI site and Sal I site is inserted into pTK that had been digested with Bam HI (and filled-in) and with Sal I. From this, a Sal I-Cla I fragment was inserted into pLNL6 digested with Sal I and Cla I.

These vectors are shown in FIG. 1, depicting the arrangement of the NeoR gene, the control element, and the HSV-TK gene. In FIG. 1, X, C, and S, identify respectively the Xho I, Cla I, and Sal I, restriction endonuclease cutting sites, which serve after filling-in as described as sites for the insertion of the various fragments into the parent plasmid pLNL6.

The abbreviations $P_{TK}$, SV and $E_I$ refer, respectively, to the HSV-TK promoter, the SV40 promoter-enhancer sequences, and the immunoglobulin heavy chain enhancer.

Other suitable vectors can be prepared by the genetic engineering techniques, such as restriction endonuclease cleavage and ligation, described above. Typically, these vectors incorporate the LTR sequences of a retrovirus and replace at least one of the genes necessary for replication of the retrovirus such as gag-pol or env with: (1) the therapeutic gene such as the HSV-TK gene operatively linked to a control element operable in mammalian cells; and (2) a selectable marker. The inserted genes, along with any remaining retroviral sequences, are then flanked by the LTR sequences.

The control element can be any eukaryotic promoter or enhancer, including for example, the Moloney murine leukemia virus promoter-enhancer element, the human cytomegalovirus enhancer, or the vaccinia P7.5 promoter. In some cases, such as the Moloney murine leukemia virus promoter-enhancer element, these promoter-enhancer elements are located within or adjacent to the LTR sequences.

The selectable marker is typically a drug-resistance marker such as kanamycin, neomycin, tetracycline, or ampicillin. These markers are generally derived from bacterial plasmids. Preferably, the incorporation of the vector as a provirus into the producer cell results in production by the cells of replication-defective infectious particles carrying the therapeutic gene free of replication-competent wild-type helper viruses.

B. Choice of Producer Cells

The choice of producer cells for implantation depends heavily on the nature of the expressed gene, characteristics of the vector and the desired phenotypic result. Because retroviral vectors are thought to require cell division and DNA synthesis for efficient infection, integration and gene expression (Weiss et al., *RNA Tumor Viruses*, 2nd Ed., Weiss et al., eds., Cold Spring Harbor Press, New York (1985)), if such vectors are used the producer cells are preferably actively growing cells such as primary fibroblast cultures or established cell lines, replicating embryonic neuronal cells or replicating adult neuronal cells in selected areas such as the olfactory mucosa and possibly developing or reactive glia. Other suitable producer cells include fibroblasts, neurons, glial cells, keratinocytes, hepatocytes, connective tissue cells, ependymal cells, chromaffin cells and other mammalian cells susceptible to genetic manipulation and grafting using the methods of the present invention. The preferred producer cells are fibroblasts. The application of methods to induce a state of susceptibility in stationary, non-replicating target cells may make many other cell types suitable targets for viral transduction. For instance, methods have been developed that permit the successful retroviral vector infection of primary cultures of adult rat hepatocytes, ordinarily refractory to infection with such vectors, and similar methods may be helpful for a number of other cells (Wolff et al., *Proc. Natl. Acad. Sci. USA* 84:3344–3348 (1987)).

For the generation of defective retroviruses carrying the HSV-TK gene, the producer cells are preferably fibroblasts or glial cells.

II. Mechanisms of Tumor Treatment Mediated by Producer Cells

When the producer cells carrying the modified retrovirus are grafted in proximity to dividing tumor cells, the tumor cells become infected with modified retrovirus carrying the therapeutic gene. Preferably, the therapeutic gene is HSV-TK, which renders cells carrying sensitive to the antimetabolite acyclovir (9-((2-hydroxyethoxy)methyl)guanine) or ganciclovir (9-((2-hydroxy-1-hydroxymethyl)ethoxy) methyl)guanine). These drugs, normally non-toxic to mammalian cells, are converted by the thymidine kinase enzyme produced by HSV-TK into intermediates that block DNA synthesis and thus prevent growth of the cells carrying them. Thus, incorporation of the HSV-TK gene presents an effective means of killing abnormally rapidly dividing cells, such as tumor cells, amidst a background of highly differentiated, essentially non-dividing cells, such as brain cells.

III. Mechanisms of Grafting Producer Cells

A. Preparation of Producer Cells for Grafting

The producer cells must be properly prepared for grafting. For example, for injection of genetically modified producer cells according to the present invention, cells such as fibroblasts obtained from skin samples are placed in a suitable culture medium for growth and maintenance of the cells, for example, a solution containing fetal calf serum and allowed to grow to confluency. The cells are loosened from the culture substrate, for example using a buffered solution such as phosphate buffered saline (PBS) containing 0.05% trypsin and placed in a buffered solution such as PBS supplemented with 1 mg/ml of glucose; 0.1 mg/ml of $MgCl_2$; 0.1 mg/ml CaCl2 (complete PBS) plus 5% serum to inactivate trypsin. The cells may be washed with PBS using centrifugation and are then resuspended in the complete PBS without trypsin and at a selected density for injection. In place of PBS, any osmotically balanced solution which is physiologically compatible with the host subject may be used to suspend and inject the producer cells into the host.

B. Preparation of Host Cells for Grafting

The host must be appropriately prepared for grafting of producer cells. This depends on the site within the host brain used for grafting. Proper blood flow and freedom from infection must be assured.

C. Grafting Mechanisms

The methods of the invention contemplate intra-cerebral grafting of producer cells containing the therapeutic gene insert, such as HSV-TK, to the region of the CNS affected by the tumor. Neural transplantation or "grafting" involves transplantation of cells into the central nervous system or into the ventricular cavities or subdurally onto the surface of a host brain. Conditions for successful transplantation include: (1) viability of the implant; (2) retention of the graft at the site of transplantation; and (3) minimum amount of pathological reaction at the site of transplantation.

Methods for transplanting various nerve tissues, for example embryonic brain tissue, into host brains have been described in *Neural Grafting in the Mammalian CNS*, Bjorklund and Stenevi, eds., (1985) Das, Ch. 3, pp. 23–30; Freed, Ch. 4, pp. 31–40; Stenevi et al., Ch. 5, pp. 41–50; Brundin et al., Ch. 6, pp. 51–60; David et al., Ch. 7, pp. 61–70; Seiger, Ch. 8, pp. 71–77 (1985); in Gage et al., *Brain Research* (1988), supra; and in co-pending U.S. patent application Ser. No. 07/285,196 by Gage, supra, incorporated by reference herein. These procedures include intra-parenchymal transplantation, i.e. within the host brain (as compared to outside the brain or extraparenchymal transplantation) achieved by injection or deposition of tissue within the host brain so as to be opposed to the brain parenchyma at the time of transplantation (Das, supra).

The two main procedures for intraparenchymal transplantation are: 1) injecting the producer cells within the host brain parenchyma or 2) preparing a cavity by surgical means to expose the host brain parenchyma and then depositing the graft into the cavity (Das, supra). Both methods provide parenchymal. apposition between the graft and host brain tissue at the time of grafting, and both facilitate anatomical integration between the graft and the region of the brain affected by the tumor.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the producer cells or by growing the cells in a substrate such as 30% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain.

The cell suspension is drawn up into the syringe and administered to anesthetized graft recipients. Multiple injections may be made using this procedure. The age of the donor tissue, i.e. the developmental stage, may affect the success of cell survival after grafting.

The cellular suspension procedure thus permits grafting of genetically modified producer cells to any predetermined site in the brain, is relatively non-traumatic, allows multiple grafting simultaneously in several different sites using the same cell suspension, and permits mixtures of cells from different anatomical regions.

For transplantation into cavities, tissue is removed from regions close to the external surface of the CNS to form a transplantation cavity, for example as described by Stenevi et al., supra, by removing bone overlying the brain and stopping bleeding with a material such a gelfoam. Suction may be used to create the cavity. The graft is then placed in the cavity. More than one transplant may be placed in the same cavity using injection of cells or solid tissue implants.

D. Level and Fidelity of Gene Expression

The level of gene expression occurring in cells infected by the defective retrovirus generated by the producer cells after transplantation must be regulated. It must be sufficiently high to ensure that the desired tumor-cell-killing effect is obtained, but must not be so high so as to be toxic to normal cells. The level of gene expression can be controlled by appropriate selection of the control elements within the defective retrovirus.

Moreover, the expression must be accurate, meaning the absence of undesired fusion products or translation of read-through transcripts. This factor can also be controlled through vector construction.

In order that the invention described may be more fully understood, the following example is set forth. It should be understood that this example is for illustrative purposes and is not to be construed as limiting the scope of this invention in any manner.

EXAMPLE I

In Vitro Gene Transfer to C6 Glial Tumor Cells

Murine retroviral vectors carrying the HSV-TK gene, the STK, NTK, and αTK vectors, were obtained from Dr. F. L. Moolten. The plasmid forms of the vectors were transfected into −2 cells (Mann et al., *Cell* 33:153–159 (1983)); selection with 1 mg/ml of the neomycin analog G418 permitted the isolation of clone producer lines that yielded viruses capable of transducing G418 resistance and HSV-TK activity. Virus titers were determined by the limiting dilution method and found to be greater than 50 pfu/cell. As expected with −2 cells, no replication-competent virus was detected.

The replicative defective viruses produced by −2 cells were used to infect C6 glial tumor cells. The cells to be infected were grown in DME plus 10% fetal bovine serum plus 4 μg/ml of polybrene and were grown to about 60–70% confluence in a T75 flask or about $2 \times 10^6$ cells/ml. The cells were infected with about 100 pfu/cell of virus. The infected cells were cultured for 24 hours with Dulbecco's Medium containing 10% fetal bovine serum and antibiotics; afterwards they were exposed to 1 mg of G418/ml to select for cells that expressed vector-derived genes.

Figure 2:
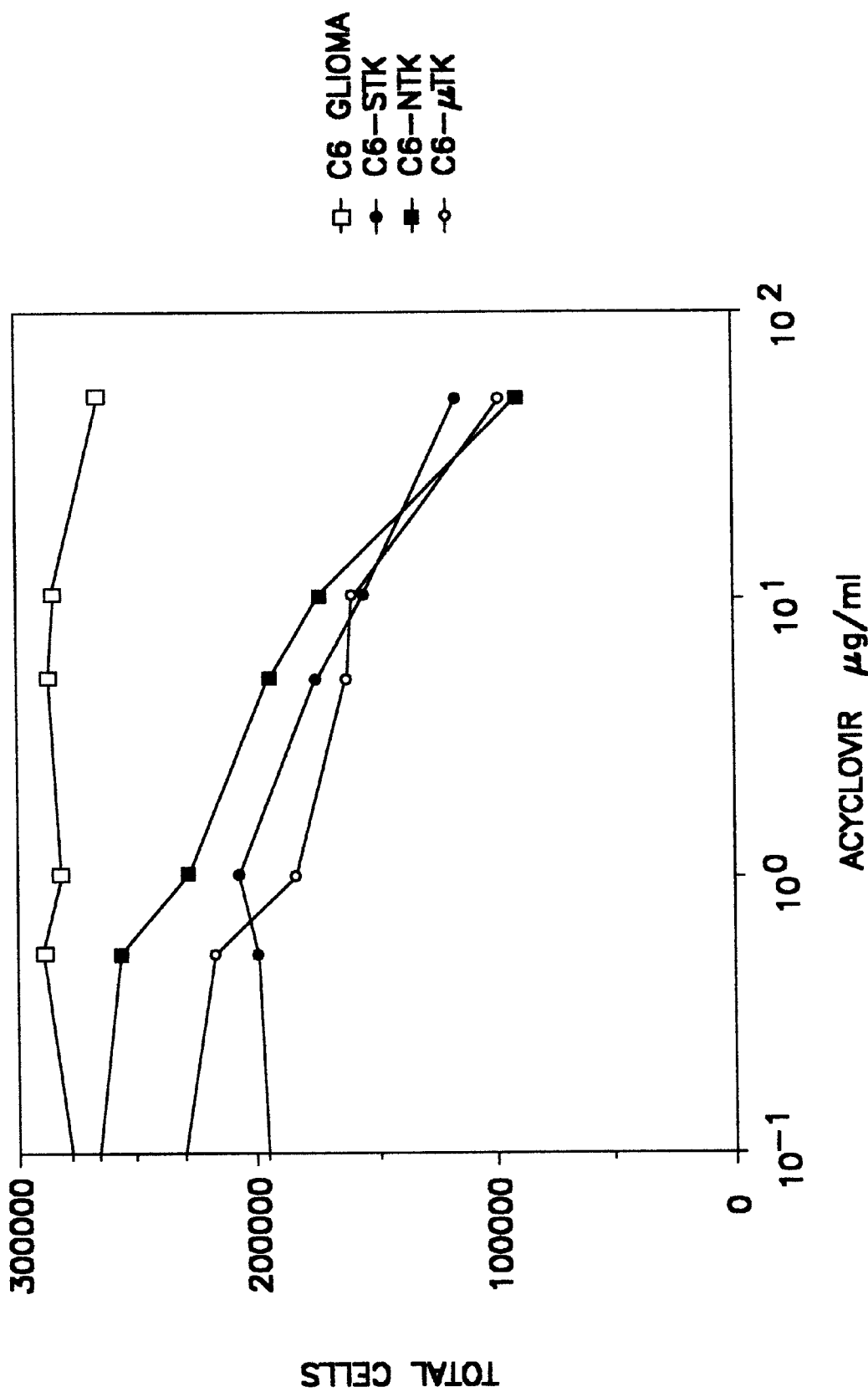
FIG. 2 is a graph showing the survival of C6 glioma cells, alone or carrying various retroviral vectors incorporating the herpes simplex virus, in the presence of increasing concentrations of acyclovir.

Clones resulting from infection of C6 glial cells with each of the vectors were exposed to acyclovir at concentrations ranging from 0.1 to 100 μg/ml for 3 days. The results are shown in FIG. 2. Each vector rendered the glial cells sensitive to acyclovir.

Similar results were obtained in a 3-day cytotoxicity assay; the inhibitory dose of acyclovir for 50% of the cells lacking the HSV-TK gene was greater-than 10 mg/ml as compared to 0.5 mg/ml for cells carrying HSV-TK.

Because normal brain cells are resistant to retroviral infection, these in vitro results suggest that genes capable of killing tumor cells can be selectively transferred to tumor cells in the brain in vivo while sparing normal cells.

EXAMPLE II

In Vivo Gene Transfer to C6 Glial Tumor Cells

Figure 3:
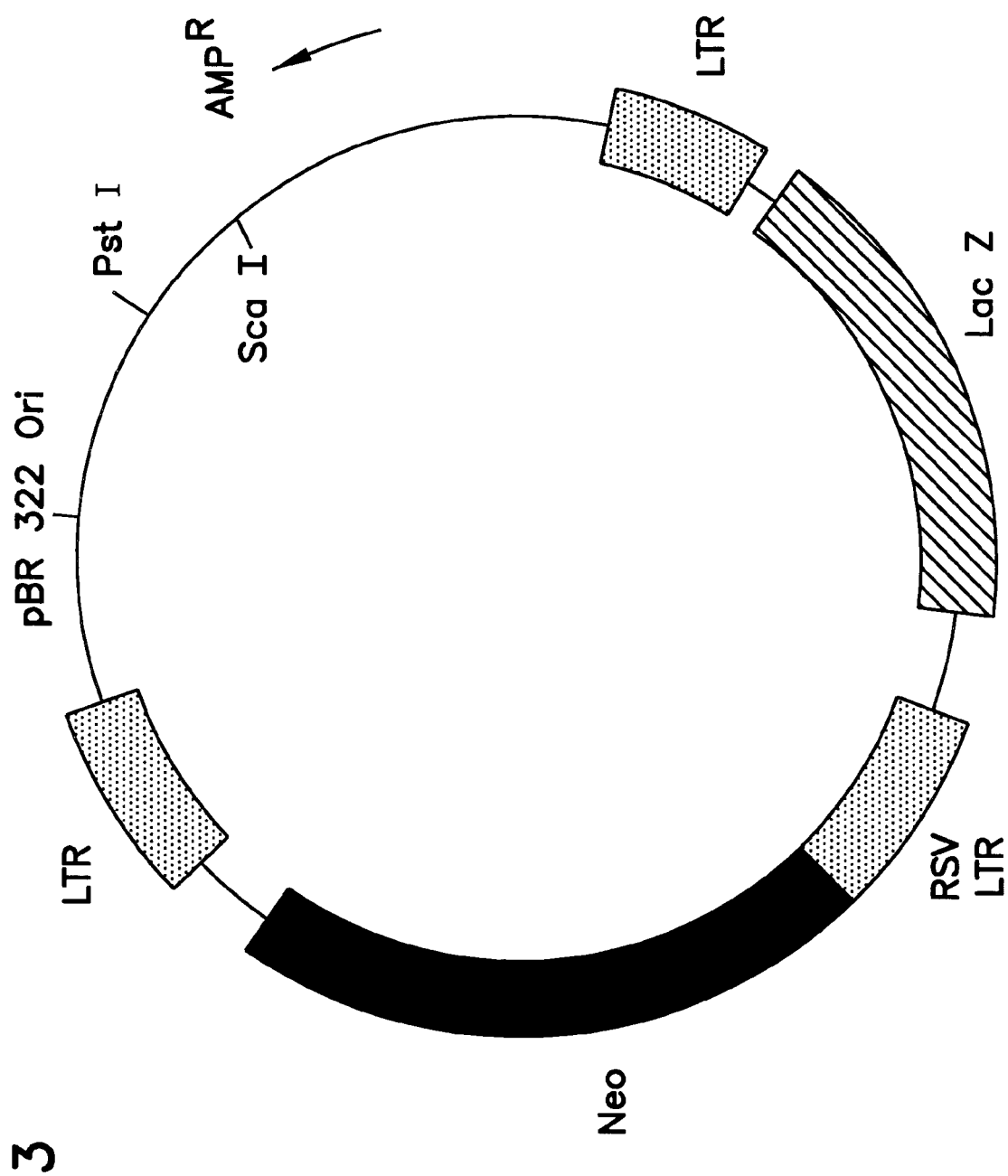
FIG. 3 is a diagram of the retrovirus-derived β-galactosidase reporter vector pLZRNL (LacZ= *Escherichia coli* β-galactosidase gene; LTR=long terminal repeat; RSV LTR=Rous sarcoma virus long terminal repeat; Neo=NeoR gene; $AMP^R$=β-lactamase gene for ampicillin selection; pBR 322 Ori=plasmid pBR 322 origin of replication).

In vivo gene transfer to C6 glial cells was demonstrated. Modified Moloney murine leukemia virus (Mo-MuLV) was used as the retroviral vector to carry out in vivo gene transfer to C6 glial tumor cells. These experiments used a vector carrying the reporter gene β-galactosidase (Zlac). The β-gal vector carried the *Escherichia coli* β-galactosidase (Zlac) gene under the control of the LTR promoter and the transposon Tn5 neomycin resistance gene (NeoR) under control of the SV 40 early promoter and was designated pLZNRL. The principal elements of this plasmid, as shown in FIG. 3, are the 3.1-kb *E. coli* β-galactosidase gene (Lac Z) under the control of Moloney murine leukemia virus LTR promoter, the neomycin resistance gene (Neo) under the control of Rous sarcoma virus LTR promoter, the β-lactamase gene (AMP$^R$) for ampicillin selection, and the plasmid origin of replication (pBR 322 Ori). Virus was generated by −2 BAG 2–14 producer cells (Shimohama et al., *Mol. Brain Res.* 5:271–78 (1989)) at greater than 50 pfu/cell. The infected cells were grown in DME with 10% fetal bovine serum plus 400 µg/ml of G418 in the presence of 10% $CO_2$.

Intracranial C6 tumors were established by the stereotaxic implantation of $10^5$ tumor cells into-the-basal ganglia of Sprague-Dawley rats under sterile conditions using a Hamilton microsyringe. One week later β-galactosidase-producer cells were injected into the intracranial tumors in concentrations of $10^6$ cells. As a control, non-virus-producing −2 were also injected into rat brain tumors. After seven days of in vivo co-incubation, animals were sacrificed and perfused with 5% paraformaldehyde. Brains and tumors were harvested and then prepared for histologic examination.

Brain sections were cut and studied using histochemical and immunohistochemical analysis to differentiate tumor cells from producer cells. Histochemical staining techniques were β-galactosidase involved incubating the brain sections with 5-bromo-4-chloro-3-indolyl-β-D-galactoside, a chromogenic substrate for β-galactosidase in a 2% solution, resulting in the development of a blue color in cells expressing the β-lac gene. Immunohistochemical techniques utilized a primary antibody against the rat brain protein nestin, which is specific for rat brain and C6 brain tumor cells. The samples were incubated with the primary antibody in 0.1 M Tris buffer plus 0.25% Triton X-100 overnight at a 1:2000 dilution of the antibody. The secondary antibody used to detect the primary antibody was FITC-labeled goat-anti rabbit IgG antibody; incubation was performed in phosphate buffered saline at pH 7.4 for 2 hours.

Previous experiments documented that C6 tumor cells and normal brain cells are both negative for β-gal. Immunohistochemical staining to determine the presence or absence of nestin showed that this protein was present in brain and C6 brain tumor cells, but absent in the −2-BAG2-14 producer cells used in this experiment. Rat brain tumor controls were negative for β-gal. Rat brain tumors injected with the β-gal retrovirus producer cells were positive for β-gal. Two types of cells were found to be positive for β-gal, cells positive for nestin, and cells negative for nestin. Somewhat less than 0.01% of the tumor cells were positive for β-gal while remaining positive for nestin. These cells are most likely tumor cells which have undergone in vivo gene transfer. These results demonstrate that in vivo gene transfer to brain tumor cells is accomplished by implantation of appropriate producer cells.

EXAMPLE III

Using the 9L experimental brain tumor model, we studied long-term regression and immunologic consequences of tumor killing in a model of in vivo gene transfer of the herpes simplex virus 1 thymidine kinase (HSV-TK) gene and ganciclovir (GCV) treatments. Fibroblasts modified to produce retroviral vectors carrying the HSV-TK gene were implanted into established 9L brain tumors in Fischer 344 rats to carry gene transfer. Animals were then treated with parenteral GCV. Significant tumor regression was seen following GCV treatments in short-term experiments (17 days) as quantified by measurements of tumor volume. In long-term studies., 7 of 32 (22%) treated animals survived 90 days. Histologic examination of the brains of the successfully treated animals demonstrated residual tumor cells and inflammatory cells consisting predominantly of macrophages/microglia and T cells in the hemisphere with the residual tumor cyst. Rats surviving 90 days rejected repeat tumor injections into the contralateral brain and flank, whereas identical tumor injections in naive animals resulted in both brain and flank tumors. The presence of significant anti-tumor immunity following HSV-TK and GCV treatments suggests that the immune system plays a critical role in the sustained tumor regressions associated with these treatments. These findings show that while HSV-TK and GCV treatments can result in long-term tumor regressions in this model, the success of these treatments could be improved by better understanding the role played by the host's immune systems.

MATERIALS AND METHODS

Retroviral Vectors and Producer Cell Lines. The producer cell lines used as the source of the retroviral vector were obtained by courtesy of Richard Mulligan of he Whitehead Institute, Cambridge, Mass. These cells were maintained in Dulbecco's modified Eagle's medium supplemented with 10% fetal bovine serum, penicillin G (100 units/ml), streptomycin sulfate (100 µg/ml), and G418 (400 µg/ml).

The pMFG-TK plasmid was constructed by cloning the MluI-Xma 1 fragment of the HSV-TK gene into the Nco I and BamHI sites of the pMFG vector (Dranoff, G., Jaffee, E., Lazenby, A., Golumbek, P., Levitsky, H. Brose, K., Jackson, V., Hamada, H., Pardoll, D. & Mulligan, R. (1993) *Proc. Natl. Acad. Sci. USA* 90, 3539–3543).

Stable ecotropic producer cell lines were generated by cotransfection of pMFG-TK and pSV2neo (Southern, P. J. & Berg, P. (1982) *J. Mol. Appl. Genet.* 1, 327–341) DNA into CRE packaging cells (Danos, O. & Mulligan, R. C. (1988) *Proc. Natl. Acad. Sci. USA* 85, 6460–6464). The recombinant MFG retrovirus produced by these cells, designated CreMoT-1.5, carries no selection gene.

Tumor Cell and Producer Cell Implantation. The 9L cells were maintained in Dulbecco's modified Eagle's medium with 10% fetal bovine serum, penicillin G (100 units/ml), streptomycin sulfate (100 µg/ml). Brain tumors were established in adult female Fischer 344 rats which were housed and handled in accordance with National Institutes of Health guidelines.

In all studies tumors were implanted by an intracerebral injection of $2\times10^5$ tumor cells into the region of the right caudate nucleus (3 mm lateral, 1 mm anterior to bregma, 4 mm ventral) (Paxinos, G. & Watson, C. (1987) *The Rat Brain in Stereotaxic Coordinates* (University Press * * *)

Animals in short-term studies underwent a second surgery 3 days after tumor implantation, at which time retroviral producer cells (either $2\times10^5$ in 4 µl or $2\times10^6$ in 8 µl, representing an equal, number (1×) or 10 times (10×) the number of injected tumor cells, respectively) were implanted into the established brain tumors and allowed to grow with brain tumor cells for 7 days. Ten days after tumor implantation, subsets of animals were given 0.2, ml intraperitoneal injections of GCV (Syntex, Palo Alto, Calif.) 50 mg/kg once a day for 7 or 14 days. Animals in the short-term experiments were sacrificed after 7 days of GCV administration (17 days after tumor implantation) and then perfused with 4% paraformaldehyde.

Two trials of long-term (90-day) survival were performed. In the first, producer cells ($2 \times 10^5$), equal to the initial number of tumor cells implanted) were grafted into 3-day-old brain tumors. GCV treatments were started in 12 animals 7 days later (tumor day 10) and continued for 7 days; 8 animals received no GCV. In the second trial, $2 \times 10^5$ or $2 \times 10^6$ producer cells in 50 $\mu$l (representing 1× or 10× the number of injected tumor cells, respectively) were grafted into 3-day-old established brain tumors of 10 animals per group. GCV treatments started 7 days later and were administered for 14 days.

Brain Tumor Analysis. Short-term treatment response was determined by comparing individual brain tumor volumes measured by postmortem stereologic study in groups containing a minimum of five animals.

Long-term results were studied in 90-day survival studies with tumor volumes determined in long-term survivors. Stained brain sections were examined and tumor volumes were quantified by stereologic methods (Gundersen, H. J. G., Bagger, P. & Bendtsen, T. F. (1988) *APMIS* * * * 96, 857–881). Tumor volumes were compared by the Mann-Whitney U test. In long-term survival experiments (90 days), animals were observed daily and survival data were analyzed by Kaplan-Meier analysis with the Mantel-Cox statistic.

Immunohistologic staining was carried out on cut brain sections to identify subsets of inflammatory cells present in the brain sections. Macrophages/microglia were identified with the antibody EDI (Chemicon, 1:100 dilution). T cells were identified with W3/13 (Sera-Lab, Crawley Down, Sussex, U.K., 1:100 dilution); OX-8 (Sera-Lab, 1:500 dilution) identified CD8-equivalent cells, and W3/25 (Sera-Lab, 1:100 dilution) identified CD4-equivalent cells. B cells were identified with OX-33 (Serotec, 1:250 dilution).

Repeat Tumor Challenge. Four animals with long-term tumor regression were studied with repeat tumor challenges 90 days after the initial tumor implantation. Animals underwent repeated intracerebral injections of $2 \times 10^5$ 9L tumor cells into the left caudate nucleus and injections of $1 \times 10^6$ 9L tumor cells into the right flank. Five normal, naive rats received identical injections of 9L tumor cells. Animals were sacrificed and perfused 17 days later to determine resulting tumor volumes.

The results of these experiments are as follows.

Figure 4:
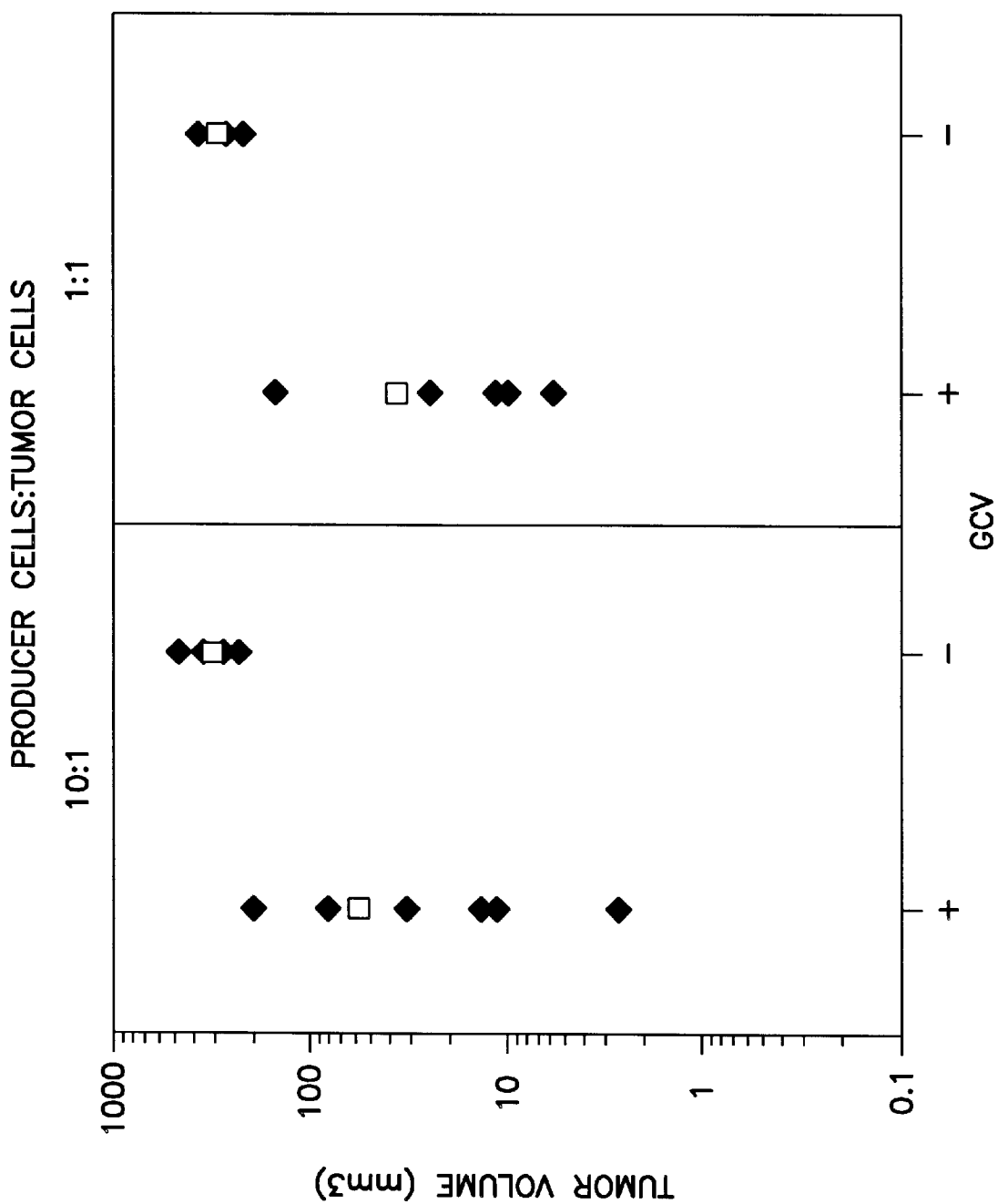
FIG. 4. Volumes of 9L brain tumors 17 days after treatment with HSV-TK retroviral producer cells and GCV. Filled symbols represent individual animals, and open squares represent the mean tumor volumes for each experimental group. Tumors were established by injection of $2\times10^5$ 9L cells in 4 μl into the right caudate nucleus. Three days later HSV-TK retroviral producer cells, $2\times10^5$(1:1) or $2\times10^6$(10:1), were implanted into the tumors and allowed to grow for 7 days; animals were then treated once a day with intraperitoneal injections-of GCV (50 mg/kg per day) for 7 days (GCV+). Control animals received injections of $2\times10^5$ (1:1) or $2\times10^6$(10:1) HSV-TK retroviral producer cells but were not treated with GCV (GCV−). Residual tumor volumes following treatments were significantly smaller (P>0.01) in those animals treated both with injections of retroviral producer cells and with GCV.
Figure 5A:
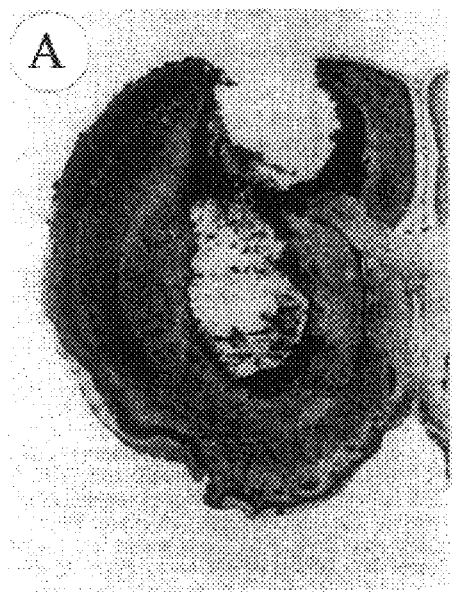
FIG. 5. Photomicrographs of 17-day-old rat brain tumors treated by implantation of HSV-TK retroviral producer cells and GCV. (A) Complete tumor regression, which was seen in 40% of animals. (B) Treatment failure, with large tumor volume with minimal evidence of tumor regression. (C and D) Local areas of tumor regression adjacent to areas of viable unaffected tumor.
Figure 5B:
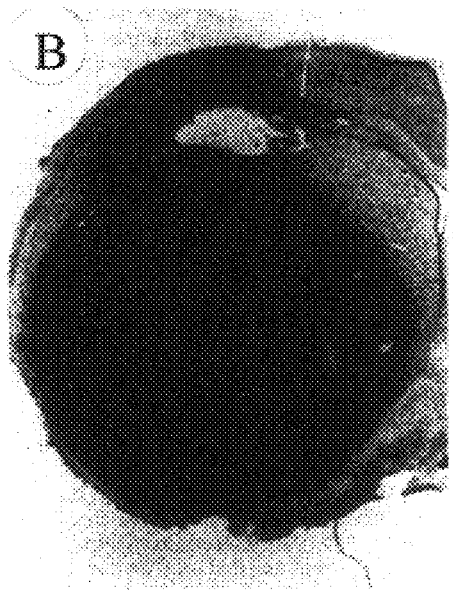
Figure 5C:
Figure 5D:
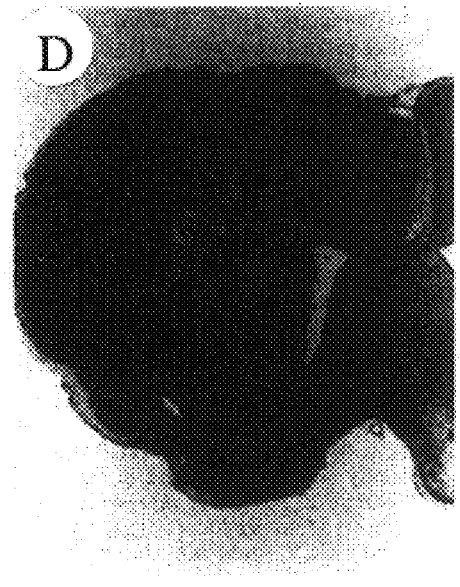

Short-Term Experiments. Tumor volumes in rats treated with GCV were significantly smaller than those in rats not treated with GCV ($P<0.01$; FIG. 4). Tumor regression was not seen in animals that received no producer cell injections but were treated with GCV (Barba, D., Hardin, J., Ray, J. & Gage, F. H. (1993) *J. Neurosurg*, 79, 729–735). Analysis of tumor response in treated animals demonstrated complete or near complete tumor regression in about 40% of treated animals; focal regression of part of the tumor adjacent to areas of unaffected tumor in about 50%, and unaffected tumors in about 10% (FIG. 5).

Figure 6A:
FIG. 6. Photomicrographs of brains from rats surviving long-term following HSV-TK producer cell implantation and GCV treatment. (A and B) Smallest and largest tumors, respectively, noted in the brains for rats 90 days following tumor implantation note the presence of the hyperchromatic cells in the small cyst in A, in contrast to the large tumor noted in B. (C and D) Smallest and largest tumors, respectively, in rats surviving 90 days following HSV-TK producer cell implantation and GCV treatment. These animals were then tested with intracerebral injections of tumor cells ($2\times10^5$ 9L cells in 4 μl) in the left hemisphere and their brains were examined 17 days later. Note the small, needle tracts and the absence of growth of injected tumor cells. Identical intracerebral injections grew large tumors in five of five naive rats.
Figure 6B:
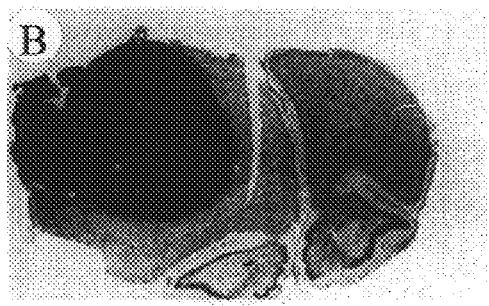

Long-Term Experiments. In the first trial, 3 of 12 treated animals survived 90 days, whereas none of 8 untreated animals survived longer than 25 days. The brains of two of the surviving treated animals showed minimal residual tumor volumes ($<0.2$ mm$^3$) in small intracerebral cysts (FIG. 6A), whereas a prominent tumor (62 mm$^3$) was seen in the third (FIG. 6B). Within the tumor, immunohistologic staining demonstrated a predominance of cells consistent with macrophages/microglia and CD8+T lymphocytes. In the brain parenchyma surrounding the residual tumor, inflammatory cells identified as macrophages/microglia by their positive stain for ED1 were also noted.

Figure 7:
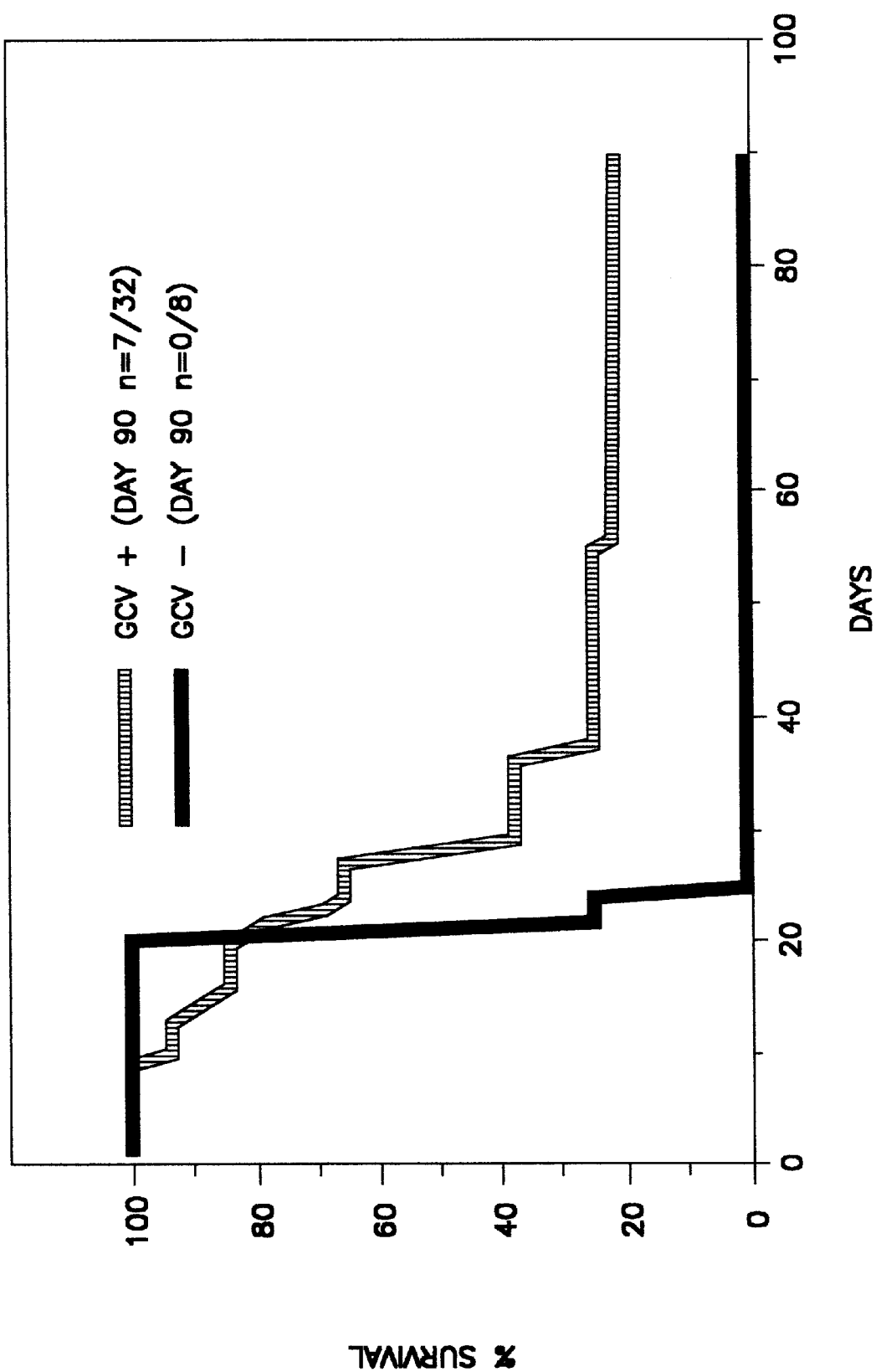
FIG. 7. Survival curve of rats with 9L brain tumors established by injection of $2\times10^5$ 9L cells in 4 μl. Treated animals (broken line) were then treated with GCV while control animals (solid line) were not treated. Animals treated with ganciclovir (+GCV) demonstrated-significant improvement in survival compared with untreated controls (7/32 treated versus 0/8 controls P<0.002).

In the second trial, after 90 days two animals in each experimental groups were alive. These four rats were designated "long-term survivors" and were studied further. No difference in survival was noted in a comparison of the treatments groups receiving 1× and 10× producer cells (both receiving GCV for 14 days). Similarly, no difference was seen between groups receiving GCV for 7 or 14 days (both receiving 1× producer cells). They were therefore combined into a single group for a comparison with the control group, which demonstrated a highly significant difference between the survival experience of treated and control animals ($P<0.002$; FIG. 7).

Figure 6C:
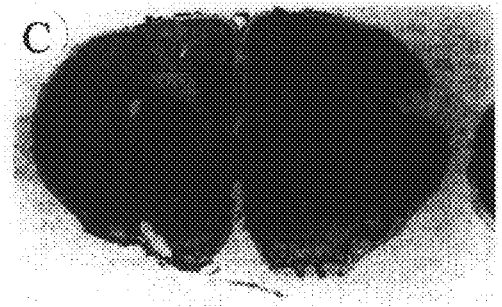
Figure 6D:
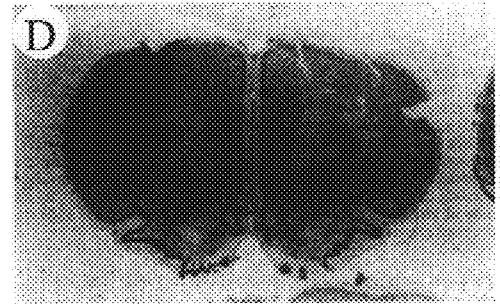
Figure 8:
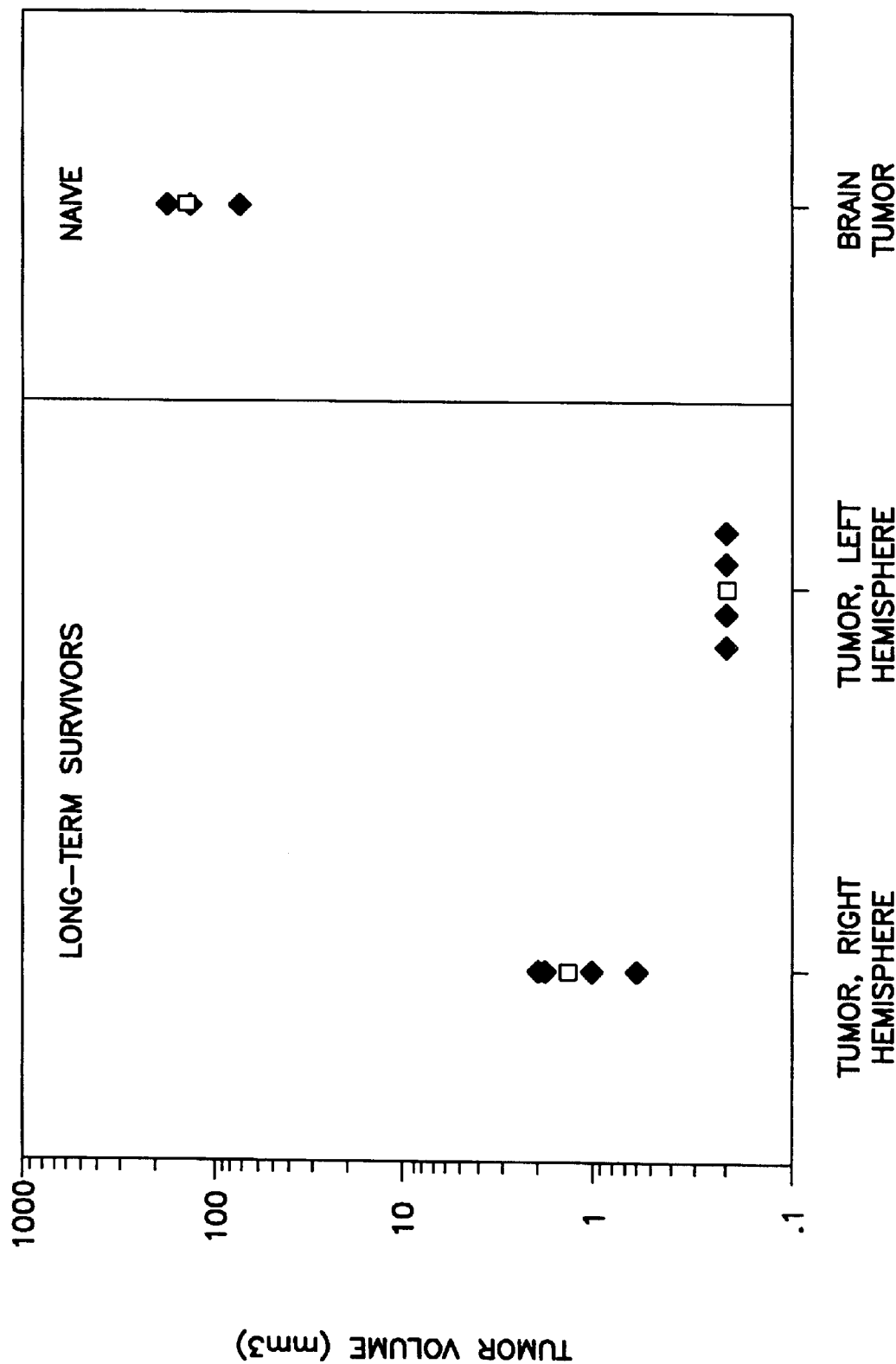
FIG. 8. Tumor volumes of rats with long-term survival following HSV-TK producer cell implantation and GCV treatment followed by repeat intracerebral tumor cell injections ($2\times10^5$ 9L cells in 4 μl) in the left hemisphere. Filled symbols represent individual animals, and open squares represent the mean tumor volumes for each experimental group. Animals were allowed to survive for another 17 days, at which time they were sacrificed and perfused and their brains were examined histologically. Note the small tumor volumes in the site of the initial tumor cell injections. At the site of the repeat tumor cell injection, there were small volume tumors demonstrating the inhibition of growth of the injected tumor cells. Identical intracerebral injections grew large tumors in five of five naive rats.

The brains of the four "long-term survivors" from the second trial which received the second tumor challenges revealed small tumor volumes (0.6–2.0 mm$^3$) composed of hyperchromatic tumor cells and small intracerebral cysts (FIGS. 6C and D) at the site of the initial tumor cell implantation. In the left hemisphere of treated animals, the site of the secondary tumor cell implants, minimal tumor volumes ($<0.2$ mm$^3$) were visible. in contrast, large brain tumors (129–169 mm$^3$) were seen in all five "naive" animals (FIG. 8; $p<0.001$). Immunohistologic studies demonstrated inflammatory cells composed primarily of macrophages/microglia and CD8+T lymphocytes in and around the small areas of residual tumor cells of the rejected tumor injections.

Detailed examination of the flanks of treated rats failed to detect any tumor nodules 17 days after tumor cell implantation, whereas large flank tumors developed in four of five naive rats after 17 days; one of the naive rats did not develop a flank tumor.

We have shown that significant anti-tumor immunity does develop following HSV-TK and GCV treatments of brain tumors. Previous studies have suggested animals treated with dexamethasone to suppress their immune systems demonstrate no reduction in the short-term success of HSV-TK and GCV treatments (5). However, the presence of residual tumor cells in the brains of the treated rats in our study which did not develop into lethal tumor burdens suggests that anti-tumor immunity present in these animals is a likely and capable participant in suppressing continued tumor growth. These residual tumor cells might also be explained by the immune privilege of the brain or by the survival of a subpopulation of tumor cells that either have a reduced growth rate or are more resistant to immune attack. Nevertheless, the presence of anti-tumor immunity, together with the finding of residual tumor cells in treated animals, supports the conclusion that the immune system participates in maintaining long-term tumor regression following HSV-TK and GCV treatments.

The experiments herein show that in vivo HSV-TK gene transfer and GCV treatment of experimental brain tumors result in short-term tumor regressions and improve long-term survival. Anti-tumor immunity develops in successfully treated animals and may play a critical role in maintaining long-term tumor regression. These strategies may also be useful against tumors of many types in other parts of the body.

It is apparent that many modifications and variations of this invention as set forth above may be made without departing from the spirit and scope of the present invention.

The specific embodiments described are given by way of example only and the invention is limited only by the terms of the appended claims.

We claim:

1. A method of transferring in vivo a tK gene into tumor cells in order to kill the tumor cells comprising:
    (a) introducing a retroviral vector into producer cells, wherein the producer cells comprise a provirus lacking a packaging signal required for encapsidation of RNA transcripts of the provirus into mature virus particles and wherein the retroviral vector comprises an intact packaging signal sequence, the retroviral vector having
        (i) the tK gene, and
        (ii) at least one gene required for replication of the retroviral vector into producer cells such that integration of the proviral DNA corresponding to the retroviral vector into the genome of the producer cells results in the generation of a modified retrovirus wherein at least one of the genes required for replication of the retroviral vector is replaced by the tK gene;
    (b) selecting producer cells from step (a) carrying the tk gene;
    (c) grafting the producer cells in proximity to the dividing tumor cells in order to infect the tumor cells with the modified retrovirus being produced by the producer cells, thereby transferring the tK gene to the tumor cells; and
    (d) killing the tumor cells by administering a substance that is metabolized by the expression product of the tk gene transferred to the tumor cells into a metabolite that kills the tumor cells.

2. The method of claim 1 wherein the tumor cells are glioma cells.

3. The method of claim 1, wherein the substance is selected from the group consisting of: 9-((2-hydroxyethoxy)methyl)guanine and 9-((2-hydroxy-1-(hydroxymethyl)ethoxy)methyl)guanine.

4. The method of claim 1, wherein the retroviral vector contains a NeoR gene and a control element selected from the group consisting of the thymidine kinase promoter, the SV40 early region promoter and enhancer, and the immunoglobulin heavy chain enhancer.

5. The method of claim 1, wherein the retroviral vector is derived from Moloney murine leukemia virus.

* * * * *